United States Patent [19]

Yoshida

[11] Patent Number: Plant 6,357

[45] Date of Patent: Oct. 25, 1988

[54] AFRICAN VIOLET NAMED ARCTIC SUN

[76] Inventor: Eiichi Yoshida, P.O. Box 4836, Hayward, Calif. 94540-4836

[21] Appl. No.: 911,644

[22] Filed: Sep. 24, 1986

[51] Int. Cl.[4] ..... A01H 5/00

[52] U.S. Cl. ..... Plt./69

[58] Field of Search ..... Plt./69

*Primary Examiner*—Robert E. Bagwill

[57] ABSTRACT

A new variety of African violets that have been bred from a hybrid formed by crossing *Saintpaulia ionantha,* the traditional florist's African violet with the high altitude species, *Saintpaulia schumensis.* The high cost of energy in northern latitudes and the relatively high temperatures required by *Saintpaulia ionantha,* which grows naturally at the foot of Mount Usamabara in East Africa, have made commercial growing of the violet expensive. By bringing in genes of *Saintpaulia schumensis* which grows at some 7,000 feet on the same mountain, which temperatures can fall as low as 55 degrees Fahrenheit, a new avenue of growth is opened up for this popular plant.

1 Drawing Sheet

BACKGROUND OF THE NEW PLANT

To obtain this new variety of African violet plant, the inventor cross-pollenated the seed parent S. 'Optimara N. Carolina' and the pollen parent *S. schumensis*×S. 'Optimara Georgia'. The seed pods of the pollenated plants were used as the generic basis for initiating further experimental series. Approximately 25 seedlings were selected by very rigid standards for further propagation. Propagation of these plants and refinement out of limited selected plants continued and tests were conducted for the development of permanent characteristics of disease resistance and vigorous growth.

DESCRIPTION OF THE PLANT

Sheet one is a full color photographic view of the plant in bloom; the colors shown being as nearly true as it is reasonably possible to obtain by conventional photographic procedures.

The following is a detailed description of my new African violet plant with the color designation being accorded to the R.H.S. Colour Chart published by The Royal Horticultural Society of London, England, with collaboration by the British Colour Council.

PLANT

Name: Arctic Sun.
Botanical classification: *Saintpaulia ionantha.*
Commercial classification: African violet.
Origin: Hybrid.
Seed parent: S. 'Optimara N. Carolina'.
Pollen parent: *S. schumensis*×S. 'Optimara Georgia'.
Form: Rosette arrangement.
Height: 6–10 cm.
Growth: Moderate, petioles at first upright, becoming horizontal with age.
Size: Medium, to 20 cm in diameter.
Mutation prone: Slight.

LEAVES

Shape: Ovate, margins slightly crenate.
Length: 6–7 cm on mature leaves.
Width: 5–6 cm on mature leaves.
Color:
*Upperside: Medium green.*

*Underside: Pale green.*
Texture:
*Upperside.*—Moderately hairy.
*Underside.*—Hairy.
Ribs and veins: Pronounced, pinnate, greenish below.
Petiole: Flattened at base, moderately hairy, purplish at first, becoming paler with age.

FLOWERS

Blooming habit: Continuous and abundant under optimal growing conditions.
Number: 3–11 per peduncle.
Size: 3–4 cm in diameter.
Color: Red-Purple (RHS 72C).
Type: Single, violet-like.
Petals: 5; margins almost entire.
Texture: Smooth, slightly flexible.
Appearance: Upperside smooth, lower side slightly pubescent.
Peduncles: 5–7 cm in height, moderately hairy, reddish green.
Inflorescence: Cyme, upright, above the foliage.
Calyx: Quinquepartite, purplish, moderately hairy.
Persistence: Flowers do not drop.
Fragrance: None.

REPRODUCTIVE ORGANS

Stamens: Two.
*Anthers.*—Bright yellow, two per filament.
*Filaments.*—c. 0.5 cm in length.
*Pollen.*—Light yellow.
Pistils: One.
*Stigma.*—Visible and accessible, becoming swollen when receptive and exuding a droplet of clear liquid.
*Style.*—c. 0.5 cm in length.
*Ovary.*—Superior.

OTHER CHARACTERISTICS

This variety will grow at lower temperatures than most commercially available hybrids because of its *Saintpaulia schumensis* parentage.

I claim:

1. An African violet plant as shown and described.

* * * * *

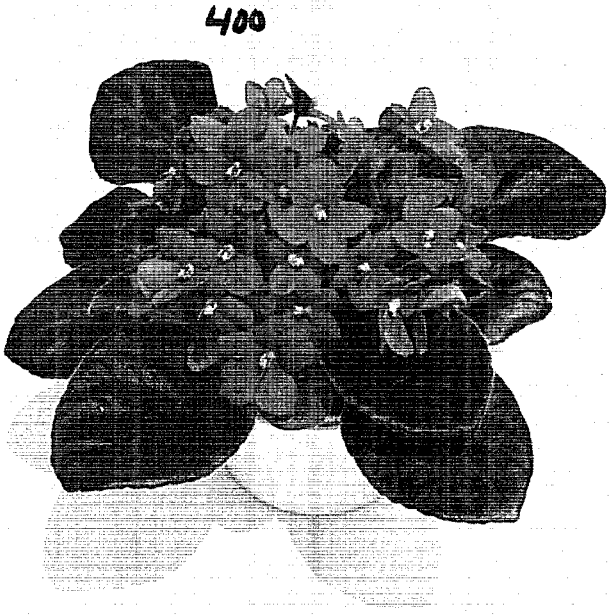
400